United States Patent [19]
Lin et al.

[11] Patent Number: 4,689,574
[45] Date of Patent: Aug. 25, 1987

[54] ELECTRON IMPACT ION SOURCE FOR TRACE ANALYSIS

[75] Inventors: Kuo-Chin Lin, Cupertino; Frederick P. Pickett, Clearlake Oaks, both of Calif.

[73] Assignee: UTI Instrument Co., Milpitas, Calif.

[21] Appl. No.: 798,007

[22] Filed: Nov. 14, 1985

Related U.S. Application Data

[62] Division of Ser. No. 472,257, Mar. 4, 1983, Pat. No. 4,579,144.

[51] Int. Cl.4 ............................................. G01N 27/62
[52] U.S. Cl. .................................... 324/464; 250/427; 324/470
[58] Field of Search ....................... 324/464, 470, 466; 250/288, 427; 313/359.1, 362.1

[56] References Cited

U.S. PATENT DOCUMENTS

| 3,050,622 | 8/1962 | Boyer et al. | 250/289 |
| 3,619,684 | 11/1971 | Andrew et al. | 315/111.31 |
| 3,648,047 | 3/1972 | Bushman et al. | 250/300 |
| 3,769,513 | 10/1973 | Delang | 250/427 X |
| 4,304,997 | 12/1981 | Sullivan et al. | 324/470 X |
| 4,315,149 | 2/1982 | Ledford, Jr. | 250/288 X |
| 4,460,317 | 7/1984 | Kern et al. | 417/49 |
| 4,529,571 | 7/1985 | Bacon et al. | 250/427 X |

Primary Examiner—Reinhard I. Eisenzopf
Assistant Examiner—Robert W. Mueller
Attorney, Agent, or Firm—Limbach, Limbach & Sutton

[57] ABSTRACT

An apparatus is disclosed for analyzing trace elements in a gas sample. A unique feedback system is provided for accurately regulating and sensing the pressure supplied to the ion chamber of the device. The feedback system is capable of compensating for a wide range of input gas pressures. The apparatus also includes an improved closed ion source which is resistant to corrosion and aids in the reduction of noise. In addition, a method is disclosed to calibrate the detector for accurately scaling the measurements of trace elements.

8 Claims, 5 Drawing Figures

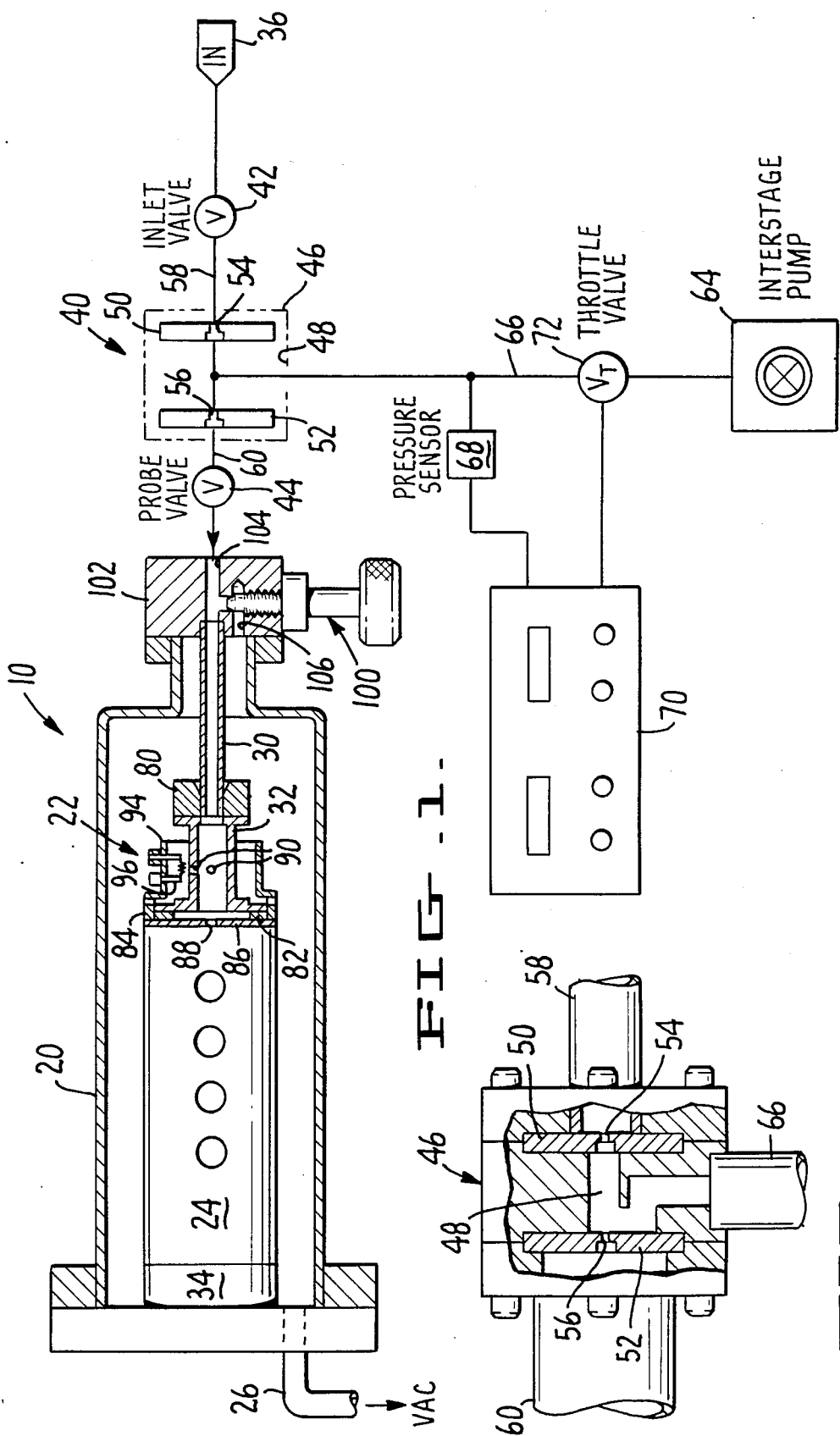

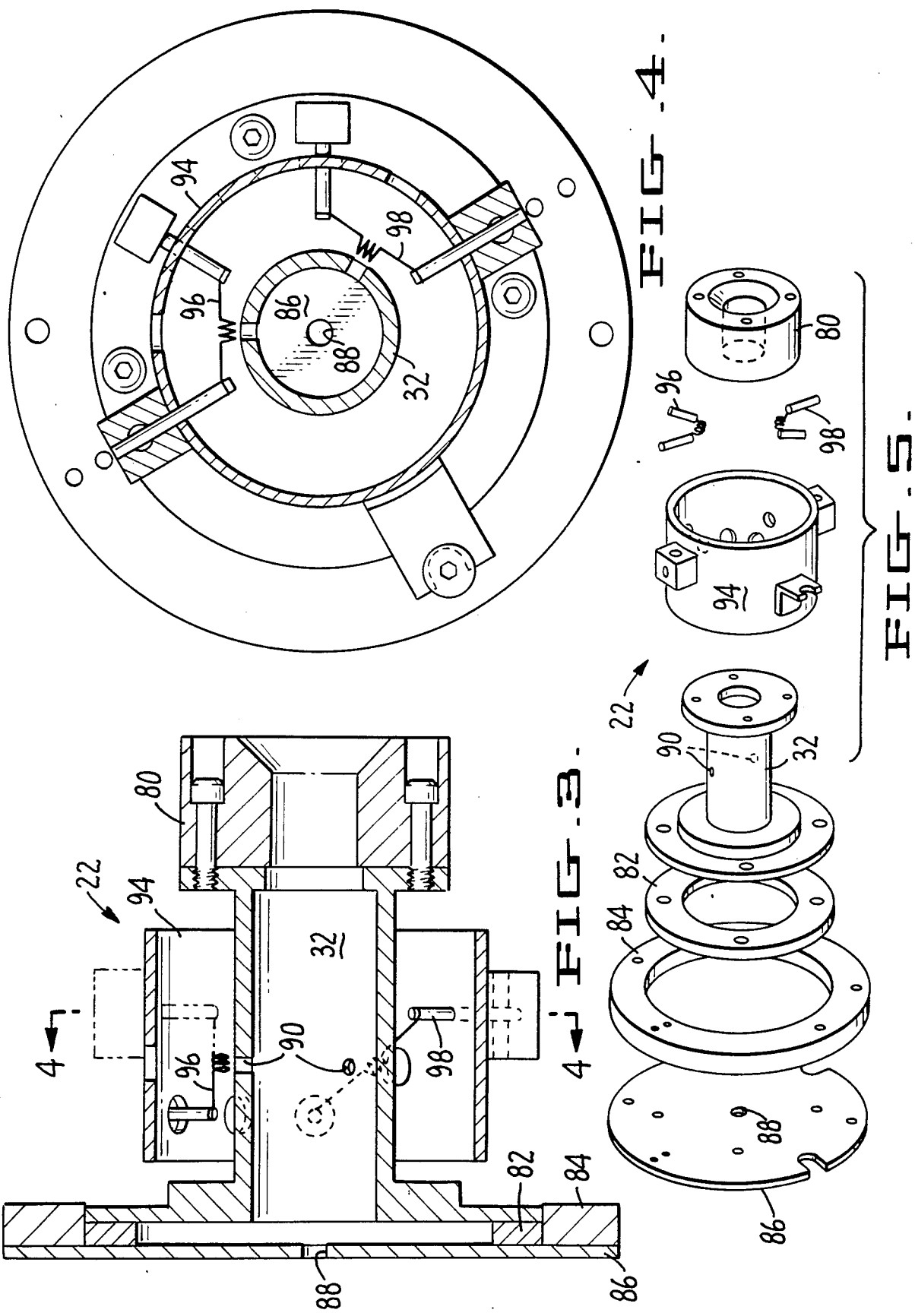

ELECTRON IMPACT ION SOURCE FOR TRACE ANALYSIS

This is a division of Application Ser. No. 472,257 filed March 4, 1983 now U.S. Pat.No. 4,579,144.

TECHNICAL FIELD

The subject invention relates to a new and improved apparatus for analyzing trace elements in a gas sample.

BACKGROUND ART

In the prior art, a variety of devices have been developed for analyzing the components in a gas sample. Among these devices are mass spectrometers and mass spectrographs each of which include three basic components, an ion source, an analyzer and a detector. In operation, a sample gas is introduced into the ion chamber. Once inside the chamber, molecules of the sample gas are ionized by any one of a variety of techniques, such as electron bombardment, photoionization, or surface emission.

The ionized molecules emitted from the chamber are introduced into some form of analyzer which separates the constitutents based on their mass. Since the particles are charged, separation can be achieved through the application of magnetic fields. Other analyzers include electrostatic and quadrupole systems. Once the ions have been separated by mass, they are detected by a sensing means, such as a multistage electron multiplier.

To date, the best known devices are capable of detecting elements in a sample having a concentration as small as a few parts per million. For a large majority of applications, this sensitivity is sufficient. However, in many fields, it is desirable to achieve even greater sensitivity. For example in semiconductor fabrication, in order to maintain high circuit quality and high yields, all gases must be certified at very high purity. More specifically, during epitaxy procedures, impurities, such as hydrocarbons or oxygen can cause formation of pits in the silicon wafer. Other applications which require reliably tested pure gases include air pollution measurements and gas chromatography systems. Accordingly, it would be desirable to provide an apparatus having enhanced sensitivity.

In order to develop an apparatus with enhanced sensitivity, a variety of problems must be overcome. One of the most significant problems relating to the detection of trace elements in a sample concerns the ability to distinguish the measured signals from background noise. As can be appreciated, when the desired signals are only marginally greater than background noise, accurate measurement is inhibited. One method of reducing background noise is to maximize the ratio between the sample gas pressure and the vacuum within the detector. At the present time, the best vacuum or base pressure which can be achieved in the detector is on the order of $10^{-8}$ torr. In contrast, sample gases are typically introduced into the ion chamber at a relatively low pressure of $10^{-6}$ torr. This low pressure is used to prevent the sample gas molecules from interacting with themselves to create dimers and trimers, rather than the monomer ions of interest. Therefore, the ratio between the sample gas pressure ($10^{-6}$ torr) and the vacuum condition at the detector ($10^{-8}$ torr) is on the order of $10^2$. This ratio results in fairly significant signal to noise errors, particularly when attempts are made to isolate trace elements in a parent gas.

Another factor which can adversely affect signal to noise ratio relates to the unwanted detection of electron and photon emissions from the ion source. In many ion sources, ions are created by impacting electrons into the gas molecules. Accordingly, a means must be provided to generate electrons and direct them into contact with the sample. For example, in a typical open bombardment source, a filament is located in contact with the sample. Electrons and photons will be emitted from the filament when it is energized. Frequently, some of these emitted electrons and photons will reach the detector and adversely effect measurement. A peripheral problem associated with this type of open source is that the sample gas tends to contaminate and corrode the filaments. Therefore it would be desirable to provide an improved ion source which reduces electron and photon noise and is less prone to corrosion.

Another difficulty encountered in trace element analysis concerns pressure measurement and regulation. More particularly, the pressure of the sample gas prior to its introduction to the testing apparatus is not constant. Typically, the sample gas pressures will vary from 0.5 atmospheres to 2.0 atmospheres. Therefore, some means must be provided for measuring the input pressure and regulating the pressure of the gas supplied to the ion source.

In the prior art, the pressure measurement problem has been addressed in two different manners, both of which have not proved to be fully satisfactory. One approach is to measure the pressure of the gas before it enters the apparatus. At this stage, when the pressure is in the atmospheric range, gases behave in a viscous manner and can be measured with relatively simple equipment. However, in the viscous condition, the movement or conductance of the sample is dependent on the viscosity of the particular gas. Accordingly, the pressure of the gas received in the ion chamber, downstream from the gas supply, will vary based on its viscosity. Thus, it is difficult to accurately calculate the pressure of the gas sample in the ion chamber based solely on the pressure at the gas supply, since the conductance of each gas sample may be different. Furthermore, the effects of viscosity will become more dominant as the distance between the gas supply and the ion chamber is increased. In the prior art, these measurement inaccuracies were often minimized by calibrating the pressure sensor based on the viscosity of the sample gas introduced into the system. This recalibration, however, is time-consuming and inefficient.

Another measurement approach is to detect the gas pressure after it has been supplied to the ion chamber and reduced to the $10^{-6}$ torr range. At this stage, the gas movement is no longer viscous, but is considered to behave in a molecular flow pattern. This approach eliminates viscous measurement problems. Unfortunately, measurements at the molecular flow level are dependent upon the size of the molecules. Therefore, even in the molecular flow range, instruments must be calibrated to account for the various size molecules in the sample gas. Accordingly, it would be desirable to come up with a pressure measurement and regulation system which minimizes the effect of viscous and molecular flow problems.

Another problem confronted when attempting to measure trace elements in a parent gas relates to the calibration of the detector. More specifically, in this region of measurement, the detector must be very finely tuned in order to provide accurate data. Calibration based on detection of expected trace elements is difficult if not impossible. Therefore, an improvement must be found to facilitate the calibration of the detector to insure accurate measurements of trace elements.

Accordingly, it is an object of the subject invention to provide a new and improved apparatus for detecting trace elements in a sample gas.

It is another object of the subject invention to provide an apparatus for detecting trace elements which includes an improved means for regulating the pressure of the sample gas introduced into the apparatus.

It is a further object of the subject invention to provide an apparatus for detecting trace elements that includes a feedback system for regulating the pressure of the sample gas that is capable of compensating for a wide range of input pressures.

It is still another object of the subject invention to provide an apparatus for detecting trace elements which includes a supply system for introducing the sample gas into the ion chamber at a known pressure.

It is still a further object of the subject invention to provide an apparatus for detecting trace elements which includes a new and improved closed ion source.

It is still another object of the subject invention to provide an apparatus for detecting trace elements which includes a new and improved closed ion source that reduces noise and resists corrosion.

It is still a further object of the subject invention to provide an apparatus for detecting trace elements that includes an improved purge system for clearing the ion source.

It is still another object of the subject invention to provide an apparatus for detecting trace elements which includes an improved calibration means.

It is still a further object of the subject invention to provide an apparatus for detecting trace elements which includes a calibration means that operates by measuring oligomers of the parent gas in order to adjust the scaling of the detector for measuring the trace elements.

DISCLOSURE OF THE INVENTION

In accordance with these and many other objects, the subject invention provides for a new and improved apparatus for detecting trace elements in a parent gas. The subject apparatus is provided with a unique gas pressure feedback system for supplying the sample gas to the testing apparatus. The apparatus also includes an unique electron impact source for ionizing the sample gas which is introduced into the ion chamber of the apparatus. Finally, a novel means is provided to calibrate the ion detector for maximizing the accuracy of the sensing of trace elements in the sample gas.

In the preferred embodiment of the subject invention, the apparatus includes a housing which is maintained at a base pressure on the order of $10^{-8}$ torr. The ion source is mounted within the housing, in communication with the input line for supplying the sample gas. A quadrupole mass analyzer and detector is mounted within the housing, downstream from the ion source, for separating and identifying the ions produced in the sample gas.

The ion source is a closed system which is operated at a pressure in excess of $10^{-4}$ torr. Preferably, pressures near $10^{-3}$ torr are utilized. This operating pressure is on the order of one hundred times greater than that commonly used in the prior art. This increase results in an increase in the base pressure ratio between the ion chamber and detector. The base pressure ratio, on the order of $10^5$, substantially enhances the signal to noise ratio in the detector, thereby improving the sensing of trace elements.

The impact ion source is defined by a generally cylindrical ion chamber having one end thereof in communication with the gas inlet line, while the other end is in communication with the quadrupole mass analyzer and detector. The chamber has at least one aperture formed therein for introducing electrons into the interior thereof. A cylindrical reflector is aligned coaxially with and disposed around the ion chamber for reflecting electrons towards the chamber. A filament means is mounted adjacent to the aperture in the chamber and between the chamber and the reflector.

In use, the filament is energized and electrons emitted therefrom enter the chamber through the aperture. Because of the closed nature of the source, corrosion problems of the filament are substantially reduced. In addition, scattering electrons and photons from the ion source are inhibited from reaching the detector thereby further reducing noise. In the preferred embodiment, a unique means is provided for purging the interior of the ion chamber.

As mentioned above, the ion source is supplied with the sample gas from a unique pressure regulation system. The pressure regulation system includes a sealed housing having an inlet opening in communication with the sample gas source line and an outlet opening in communication with the ion chamber.

The system further includes a sensor means for measuring the gas pressure within the housing. A pump means is also provided for regulating the pressure in the housing by evacuating the sample gas therefrom. Finally, a control means is connected to the pressure sensor and the pump means for regulating the pressure in the housing.

The subject regulation systems takes advantage of two physical phenomena in order to provide accurately regulated gas pressure in the ion chamber. The first effect concerns the passing of a gas through a narrow aperture. More particularly, when a gas passes through an aperture into a sealed chamber, a known pressure reduction occurs, which is dependent on the size of the aperture. Thus, if the pressure within the housing is known, and the diameter of the outlet opening in the housing is also known, the pressure supplied to the ion chamber can be calculated. Therefore, if the pressure in the chamber can be accurately measured, the pressure in the ion chamber can be accurately calculated.

The second consideration concerns the measurement of low pressure gases. As pointed out above, there are difficulties encountered in measuring gases in either the viscous or molecular flow stage. These difficulties are substantially minimized in the subject invention. In the preferred embodiment, gas pressure measurements are taken in the regulator housing where a pressure of approximately one torr is maintained. At this stage, the gas still behaves in a viscous manner, permitting measurement with relatively simple equipment. However, the problems associated with viscous pressure measurement are substantially minimized. More particularly, in the subject system, the sample gas experiences a sharp pressure change as it exits the housing, from one torr down to approximately $10^{-3}$ torr. The rapid transition to the molecular flow range functions to sharply reduce the length of the viscous flow path. By this arrangement, inaccuracies resulting from differing conductance levels of each type of gas are reduced, permitting pressure measurements without the need to recalibrate the instruments for each sample.

The subject invention further includes a unique means for calibrating the detector. As pointed out above, the pressure in the ion source is to be maintained in excess of $10^{-4}$ torr. At this level, the parent gas will tend to form dimers and trimers (generically oligomers) of the parent gas molecules. In the prior art, this result was undesirable since the devices were attempting to measure the constituents of the parent gas. However, in the subject apparatus, the intent is to analyze trace elements, which are present in such minute amounts than only monomer ions of the trace elements will be found. In fact, the presence of parent gas oligomers, rather than being undesirable, is used beneficially to aid in the calibration of the detector. As discussed more fully hereinbelow, where the pressure in the ion chamber is accurately known, the level of oligomers produced can be accurately calculated. Further, since the level of oligomers actually produced is significantly higher than the trace element ions, the oligomers can be readily measured by the detector. In operation, the detector is adjusted such that the actually measured level of oligomers corresponds to the calculated level whereby the subsequently measured levels of trace elements in the sample will be accurately scaled.

Further objects and advantages of the subject invention will become apparent from the following detailed description taken in conjunction with the drawings in which:

BRIEF DESCRIPTION OF THE DRAWINGS

FIG. 1 is a partial cross-sectional view, including block diagrams, of the apparatus for detecting trace elements in accordance with the subject invention.

FIG. 2 is a cross-sectional view of the housing module of the pressure regulating means of the subject invention.

FIG. 3 is an enlarged, cross-sectional view of the electron impact ion source of the subject invention.

FIG. 4 is a cross-sectional view of the electron impact ion source of the subject invention, taken along the line 4—4 of FIG. 3.

FIG. 5 is an exploded perspective view of the electron impact ion source of the subject invention.

BEST MODE FOR CARRYING OUT THE INVENTION

Referring to FIG. 1, there is illustrated an overall view of the apparatus 10 for detecting trace elements in accordance with the subject invention. Briefly, the analyzer includes a sealed, main housing 20 for containing the ion source 22 and the analyzer 24. The interior of the housing 20 is evacuated by a pump (not shown) through a vacuum line 26. As discussed below, it is desirable to maintain the vacuum created therein as complete as possible. In the preferred embodiment, the base pressure within the housing is on the order of $10^{-8}$ torr.

The housing 20 includes a main inlet tube 30 for receiving the sample gas. The sample will pass through tube 30 and into the ion chamber 32. Molecules of the sample gas are then ionized and pass into the analyzer 24. While a variety of analyzers are suitable for use with the subject invention, in the preferred embodiment, a quadrupole mass analyzer is used. In a quadrupole mass analyzer, a DC and superimposed RF voltage field is established between a rectangular array of elongated rods in a manner to filter the ionized molecules in accordance with the charge to mass ratio of the molecules. In this manner, a mass spectrum is produced of the ionized material at the output of the analyzer. This output is supplied to a detector 34. In the preferred embodiment, detector 34 is defined by a multistage electron multiplier and Faraday cup combination.

The sample gas to be tested is supplied to the apparatus 10 from a source 36. Interposed between the housing 20 and the source 36 is a unique means 40 for accurately regulating the pressure of the sample gas introduced into the ion chamber 32. As will be appreciated from a full discussion of the invention, the accurate regulation of the sample gas pressure greatly facilitates the ability of the device to measure trace elements in the sample gas. A pair of valves 42 and 44 may be provided on either side of the pressure regulation means 40 for isolation purposes.

As discussed above, the gas pressure of the source 36 will typically vary over a range of 0.5 atmospheres to 2.0 atmospheres. It is necessary that the regulation means 40 be able to compensate for this wide range of input pressures. Further, the regulation means must also be able to accurately measure and deliver the desired pressure of the sample gas to the ion chamber 32.

Referring now also to FIG. 2, the pressure regulation means of the subject invention will be discussed in greater detail. More specifically, pressure regulation means 40 includes a housing module 46 having an open interior 48. Module 46 further includes a pair of opposed walls 50 and 52 having apertures 54 and 56, located therein. Aperture 54 is in communication with input line 58 from the gas supply source 36. Aperture 56 is in communication with output line 60 for channeling the gas to the ion chamber 32.

In accordance with the subject invention, a pump 64 is provided for regulating the pressure within the module 46 by evacuating gas therefrom. Pump 64 is connected to the module via line 66. In addition, a pressure sensor 68 is provided for monitoring the pressure within module 46. Finally, a control means, illustrated generally at 70, is provided which is operatively connected to the sensor 68 and the pump 64. Preferably, the control 70 is connected to pump 64 via throttle valve 72. As will be discussed below, control means 70 functions to actuate throttle valve 72 enabling pump to regulate the pressure within module 46 in response to sensor 68. By this arrangement, the pressure of the gas sample supplied to the ion chamber 32 can be accurately regulated.

As discussed above, the subject regulation system takes advantage of two physical phenomena. The first concerns the behavior of gases when they pass through a relatively small aperture. More particularly, when a gas passes through a small aperture, it will experience a fixed pressure drop. Therefore, when the size of the aperture is known, and the pressure on the upstream side of the aperture is also known, the pressure on the downstream side of the aperture can be calculated. This principle is used to calculate the pressure leaving module 46 and supplied to ion chamber 32. Stated differently, since the size of aperture 56 is known, the pressure within module 46 can be regulated to insure a known gas pressure in the ion chamber.

As can be appreciated, in order for the above calculations to be accurate, the pressure within module 46 must be accurately determined. This result is achieved by taking advantage of the second physical principle. More particularly, and as discussed below, because the pressure in module 46 is maintained in the viscous region (about 1 torr), highly accurate measurements can be taken using a relatively simple capacitance manometer sensor without having to recalibrate for each individual gas sample. As pointed out above, a gas which is maintained at a relatively low pressure, on the order of $10^{-4}$ torr, exhibits molecular flow characteristics. At this stage, the size of the gas molecules must be considered during measurement. In contrast, measurements can more easily be made in the viscous region. However, because the conductance of each gas varies with its viscosity, measurement inaccuracies can arise, particularly where the flow path between the gas supply and the ion chamber is long.

These problems are overcome in the subject invention by measuring the pressure at an interstage level. Since this level is in the viscous range, pressure measurements are relatively simple. In addition, the sample gas experiences a sharp pressure drop, across wall 52, down to approximately $10^{-3}$ torr. This rapid transition to the molecular flow range functions to sharply reduce the length of the viscous flow path. By this arrangement, problems associated with different conductance levels are minimized, alleviating the need for frequent recalibration of the sensor. Since accurate pressure measurements may be made within the module, the pressure within the ion chamber 32 can be accurately calculated.

Having described the principles of the regulation system 40, its operation will now be explained. In use, control means 70 is programmed to maintain the pressure within the module 46 at a specific level. This level is based upon the desired pressure level in the ion chamber 32. Sample gases are introduced into module 46 from source 36 and through valve 42. As discussed above, the pressure of the source will typically range between 0.5 atmospheres to 2.0 atmospheres. Pressure sensor 68 monitors the pressure within module 46. Whenever this pressure begins to exceed the desired level, control means 70 actuates throttle valve 72 in a manner to connect pump 64 to the interior of module 46. Pump 64 draws off a portion of the sample gas until the pressure within the module 46 is reduced to the desired level. The accuracy of the subject feedback system also enables detector 34 to be accurately calibrated, as discussed more fully hereinbelow.

Once the sample gas exits aperture 56 of the chamber it will move into line 60 through probe valve 44 and into ion chamber 32 via line 30. Preferably, the pressure in ion chamber 32 is on the order of $10^{-3}$ torr. As pointed out briefly above, ion source 22 is relatively corrosion free and also functions to significantly reduce noise often created in prior art devices by stray electrons and photons.

The advantages of ion source 22 can best be appreciated by referring to FIGS. 3 through 5. Ion source 22 consists of a generally cylindrical ion chamber 32 formed from stainless steel or other non-corrosive material. The upstream end of ion chamber 32 is mounted to a ceramic dielectric cylinder 80. As illustrated in FIG. 1, cylinder 80 receives input line 30. The downstream end of chamber 32 is mounted to the analyzer 24. Interposed between the analyzer and the chamber 32 are a pair of ceramic insulating rings 82 and 84. In addition, a metallic focus plate 86 is mounted against the upstream end of analyzer 24 and includes a central aperture 88 for emitting ions into the analyzer.

In accordance with the subject invention, ion chamber 32 includes a pair of apertures 90 for emitting electrons into the interior of the chamber. A generally cylindrical electron reflector 94 is mounted coaxially about ion chamber 32. As illustrated in FIGS. 3 and 4, a pair of filaments 96 and 98 are mounted adjacent the apertures in the ion chamber 32. In use, a current is passed through filaments 96 and 98 such that they emit electrons. Because of their location, a large portion of the electrons emitted from the filaments will enter the ion chamber through apertures 90. To further insure that the electrons are directed towards the chamber, reflector 94 is preferably maintained at a negative bias voltage, on the order of 50 volts.

In operation, a sample gas is introduced into the ion chamber through conduit 30. The sample gas molecules are then subjected to electron bombardment from filaments 96 and 98. This bombardment ionizes a percentage of the molecules in the sample gas. Molecules of the sample gas then move through aperture 88 in focus plate 86 and into the quadrupole analyzer 24.

As discussed above, the design of the subject ion source 22 is intended to reduce noise and be corrosion resistant. As can be appreciated, due to the relatively restricted apertures 90 in ion chamber 32, few gas molecules will escape therefrom. Accordingly, corrosion and contamination of the filaments and reflector is substantially reduced. In addition, due to the relatively small aperture 88 in focus plate 86, only a limited amount of free electrons and photons emitted from the filament will enter the analyzer 24. In this manner, spurious noise is reduced.

Another feature of the ion source includes a means for cleansing the system of any residual matter. Frequently, during the operation of the apparatus, polar gas molecules will tend to cling to the walls of the ion chamber 32. This contamination can affect the accuracy of the trace element analysis.

Accordingly, it would be desirable to provide a means to purge the system on a periodic basis to remove the residual contaminating molecules. This object is achieved by a valve means 100. As illustrated in FIG. 1, an outer mounting block 102 is connected to the upstream end of housing 20. Block 102 includes a main channel 104 for receiving the sample gas. Block 102 further includes an L-shaped side channel 106 which is in communication with both the main channel 104 and the interior of housing 20. When valve means 100 is in the closed position, as illustrated in FIG. 1, the sample gas will pass directly from module 46 along channel 104 and into the ion chamber 32. However, when the system is to be cleansed, the probe valve 44 is initially closed and valve 100 is opened. In this orientation, the main channel 104 is exposed to the high vacuum contained in housing 20. The high vacuum condition functions to evacuate all residual molecules clignging to the interior surface of the ion chamber 32. Preferably, the evacuation purge system is supplemented by a heating source for baking the residual contaminating molecules. The heating source (not shown) can be mounted about the reflector 94.

Having described the operation of the ion source, the calibration system of the subject invention will now be described. As pointed out above, the subject apparatus is intended to detect trace elements in a parent gas having a density of one part per million or less. It is extremely difficult, if not impossible, to calibrate detection equipment at these extremely low levels. Accordingly, the subject apparatus includes an alternate calibration method which enables the accurate measurement of the trace elements.

In the prior art devices, sample gas pressures in the ion source were typically maintained at a level of $10^{-6}$ torr. At this level, the primary ionization mode of the parent gas was through the bombardment of electrons. If the gas pressures are raised much higher, the sample gas molecules tend to interact between themselves, creating multiple dimer and trimer (generically, oligomer) ions. Since these dimers and trimers would form a significant portion of the sample, the background noise created therefrom would adversely affect measurement.

As discussed above, in the subject invention, the pressure in the ion chamber is intended to be maintained at approximately $10^{-3}$ torr. As can be appreciated, this pressure will create significant dimer and trimer ions of the parent gas. However, because of the relatively low percentage of trace elements in the sample (and therefore low partial pressure), there is almost no formation of trace element oligomers. This condition is taken advantage of in the subject invention.

The level of oligomer production of the parent gas within the sample chamber is directly proportional to the pressure within the chamber. Accordingly, if the pressure in the chamber can be accurately measured, the level of oligomer production can be calculated. Since, the subject invention provides an unique means for accurately determining the pressure within the ion chamber, the resulting oligomer production can be accurately calculated.

In operation, the detector is tuned to sense the actual oligomers produced. The detector is then calibrated such that the actual level of oligomers measured matches the calculated value based on the pressure within the ion chamber. Having scaled the detector, the analyzer can then accurately isolate trace elements. Operated in accordance with this method, the subject apparatus is capable of detecting trace elements having a concentration of less than one part per million.

In summary, there has been disclosed a new and improved apparatus for detecting trace elements in a parent gas sample. The subject apparatus includes an unique feedback system for accurately regulating and sensing the pressure supplied to the ion chamber. The feedback system is capable of compensating for a wide range of input gas pressures. An improved closed ion source is also disclosed which is resistant to corrosion and aids in the reduction of noise. In the preferred embodiment, an improved purge system is provided for evacuating the ion chamber. Finally, an improved method and means for calibrating the detector of the apparatus is disclosed. In the subject method, the expected level of parent gas oligomers are calculated based on the pressure within the ion chamber. The detector is then calibrated such that the actual level of oligomers sensed corresponds to the calculated value. By this arrangement, the measurements of the trace elements can be accurately scaled.

While the subject invention has been described with reference to a preferred embodiment, it is to be understood that various other changes and modifications could be made therein by one skilled in the art, without varying from the scope and spirit of the subject invention as defined by the appended claims.

We claim:

1. An electron impact ion source for use in a trace analysis apparatus, said apparatus including a housing having an analyzing means disposed therein, said apparatus further including an input line for supplying a gas to be tested, said ion source being interposed between said input line and said analyzing means and comprising:

an ion chamber having one end thereof in communication with said input line and with an other end of said chamber being in communication with said analyzing means, said chamber having at least one aperture formed therein for introducing electrons into an interior of said chamber;

a reflector aligned coaxially with and disposed around said chamber;

filament means, located between said chamber and said reflector, far emitting electrons, whereby in use, electrons emitted by said filament enter said chamber through said aperture such that gas supplied to said chamber can interact with said electrons to produce ions; and a focus plate interposed between said ion chamber and said analyzing means, said focus plate having an aperture therein for emitting ions into said analyzing means, said focus plate also functioning to inhibit electrons and photons from entering said analyzing means.

2. An ion source as recited in claim 1 wherein said filament means is aligned with said aperture in said chamber.

3. An ion source as recited in claim 1 wherein said chamber includes two apertures and said filament means is defined by a pair of filament members respectively aligned with said apertures in said chamber.

4. An ion source as recited in claim 1 wherein said filament means is mounted to said reflector.

5. An ion source as recited in claim 1 wherein said reflector is negatively charged to facilitate a repulsion of electrons towards said ion chamber.

6. An ion source as recited in claim 1 further including a means for evacuating said chamber to facilitate purging of all residual materials held therein.

7. An ion source as recited in claim 6 wherein the interior of the housing of said analysis apparatus is maintained in a near vacuum conditions and said means for evacuating said chamber includes a means for exposing said chamber to said near vacuum.

8. An ion source as recited in claim 7 wherein said means for exposing said chamber to said near vacuum in said housing includes a valve means interposed between and in communication with both said input line and said housing such that when said valve means is opened, said chamber is exposed to the near vacuum within the housing for purging any residual matter remaining in said ion chamber.

* * * * *